United States Patent [19]
Polarek et al.

[11] Patent Number: 5,510,328
[45] Date of Patent: Apr. 23, 1996

[54] COMPOSITIONS THAT INHIBIT WOUND CONTRACTION AND METHODS OF USING SAME

[75] Inventors: James Polarek, Del Mar; Richard Tamura, San Diego; John Harper, Carlsbad, all of Calif.

[73] Assignee: La Jolla Cancer Research Foundation, La Jolla, Calif.

[21] Appl. No.: 234,979

[22] Filed: Apr. 28, 1994

[51] Int. Cl.$^6$ ............................. A61K 38/16; C07K 7/08
[52] U.S. Cl. .................................. 514/8; 514/14; 514/16; 514/17; 530/326
[58] Field of Search ................................. 514/8, 14, 16, 514/17; 530/326

[56] References Cited

U.S. PATENT DOCUMENTS

| | | | |
|---|---|---|---|
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,792,525 | 12/1988 | Ruoslahti et al. | 435/240.24 |
| 5,041,380 | 8/1991 | Rouslahti et al. | 435/240.2 |

FOREIGN PATENT DOCUMENTS

WO9006767  6/1990  WIPO.

OTHER PUBLICATIONS

Schreiber, Ronda E. "Reversal of RGD Peptide–Mediated Wound Contraction Enhancement by Incorporation of a Poly–Cationic Sequence." Wounds 6:72 (1994).

Harper, John "The Role of TGF–$\beta$ and Decorin in Controlling Fibrosis." Wounds 6:70 (1994).

Kresse, H. et al., "Biosynthesis and Interactions of Small Chondrotin/Dermatan Sulphate Proteoglycans." Eur. J. Clin. Chem. Clin. Biochem. 32:259–264 (1994).

Brown, David C. and Vogel, Kathryn G. "Characteristics of the In Vitro Interaction of a Small Proteoglycan (PG11) of Bovine Tendon with Type 1 Collagen." Matrix 9:468–478 (1989).

Vogel, Kathryn G. et al., "Specific Inhibition of Type I and Type II Collagen Fibrillogenesis by the Small Proteoglycan of Tendon." Biochem. J. 223:587–597 (1984).

Greve, Herman et al., "Influence of Collagen Lattice on the Metabolism of Small Proteoglycan II by Cultured Fibroblasts." Biochem. J. 269:149–155 (1990).

Ruoslahti, Erkki, "Structure and Biology of Proteoglycans." Ann. Rev. Cell. Biol. 4:229–255 (1988).

Vogel, Kathryn G. and Trotter, John A. "The Effect of Proteoglycans on the Morphology of Collagen Fibrils Formed in Vitro." Collagen Rel. Res. 7:105–114 (1987).

Polarek, James W. et al., "Development of a Provisional Extracellular Matrix to Promote Wound Healing." Wounds 6:46–53 (1994).

Guidry, Clyde and Grinnell, Frederick "Heparin Modulates the organization of Hydrated Collagen Gels and Inhibits Gel Contraction by Fibroblasts." J. Cell Biol. 104:1097–1103 (1987).

Agrez, M. V. and Chua, F. K. "The Role of Colon Fibroblasts in Malignant Large Bowel Obstruction–an Experimental in Vitro Model." Br. J. Cancer. 62:567–572 (1990).

Gullberg, Donald, et al., "$\beta_1$ Integrin–Mediated Collagen Gel Contraction is Stimulated by PDGF." Experimental Cell Res. 186:264–272 (1990).

Guidry, Clyde and Grinnell, Frederick "Studies on the Mechanism of Hydrated Collagen Gel Reorganization by Human Skin Fibroblasts." J. Cell Sci. 79:67–81 (1985).

Staatz, William D. et al., "The $\alpha_2\beta_1$ Integrin Cell Surface Collagen Receptor Binds to the $\alpha 1(I)$–CB3 Peptide of Collagen." J. Biol. Chem. 265:4778–4781 (1990).

Donaldson, Donald J. and Mahan, James T. "Newt Epidermal Cell Migration In Vitro and In Vivo Appears to Involve Arg–Gly–Asp–Ser Receptors." J. Cell Science. 87:525–534 (1987).

Smith, Daniel J. et al., "Video Image Analysis of Wound Repair." Wounds 4:6–15 (1992).

Burgess, Maria Lonnett et al., "Integrin–Mediated Collagen Gel Contraction by Cardiac Fibroblasts." Circulation Res. 74:291–298 (1994).

Debhar, Shoukat et al., "A Cell Surface Receptor Complex for Collagen Type Recognizes the Arg–Gly–Asp Sequence." J. Cell Biol. 104: 585–593 (1987).

Agrez, Michael V. et al., "Arg–Gly–Asp–Containing Peptides Expose Novel Collagen Receptors on the Fibroblasts: Implications for Wound Healing." Cell Regulation 2:1035–1044 (1991).

Tomasek, James J. and Akiyama, Steven K. "Fibroblast–Mediated Collagen Gel Contraction Does Not Require Fibronectin–$\alpha_5\beta_1$ Integrin Interaction." Anatomical Record 234:153–160 (1992).

Cardarelli, Pina M. et al., "The Collagen Receptor $\alpha 2\beta 1$, from MG–63 and HT1080 Cells, Interacts with a Cyclic RGD Peptide" J. Biol. Chem. 267:23159–23164 (1992).

Albina, Jorge E. et al., "Regulation of Macrophage Functions by 1–Arginine." J. Exp. Med. 169:1021–1029 (1989).

Albina, Jorge E. et al., "Arginine Metabolism in Wounds." Am. J. Physiol. 254:E459–E467 (1988).

Albina, Jorge E. et al., "Temporal Expression of Different Pathways of 1–Agrinine Metabolism in Healing Wounds." J. Immun. 144:3877–3880 (1990).

(List continued on next page.)

*Primary Examiner*—Jill Warden
*Assistant Examiner*—Benet Prickril
*Attorney, Agent, or Firm*—Campbell and Flores

[57] ABSTRACT

The present invention provides methods for reducing or inhibiting wound contraction in a subject having a wound comprising administering to the subject a pharmaceutical composition comprising a peptide or a polypeptide. The invention provides, for example, a method of reducing or inhibiting wound contraction comprising the administration of a pharmaceutical composition comprising a peptide having more than three consecutive basic amino acids. The invention also provides a method of reducing or inhibiting wound contraction comprising the administration of a pharmaceutical composition comprising decorin.

2 Claims, 4 Drawing Sheets

OTHER PUBLICATIONS

Barbul, Adrian et. al., "Intravenous Hyperalimentation with High Arginine Levels Improves Wound Healing and Immune Function." J. Surgical Res. 38:328–334 (1985).

Mills, Charles D. et al., "Concomitant Macrophage Activation and Fibroblast/Lymphocyte Inhibition by Wound Fluid: The Arginine–Deficiency of Inflammation is" a Partial Explanation. Clinical and Experimental Approaches to Dermal and Epiderman Repair: Normal and Chronic Wounds, p:193–203 Wiley–Liss, Inc. (1991).

Grinnell, Frederick et al., "The Collagen Recognition Sequence for Fibroblasts Depends on Collagen Topography." Experimental Cell Res. 182:668–672 (1989).

Grinnell, Frederick "Mini–Review on the Cellular Mechanisms of Disease: Fibroblasts, Myofibroblasts and Wound Contraction." J. Cell Biol. 124:401–404 (1994).

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 12 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

Tyr Gly Arg Arg Arg Arg Arg Gln Arg Arg Arg Pro
   1               5                   10

( 2 ) INFORMATION FOR SEQ ID NO:2:

( i ) SEQUENCE CHARACTERISTICS:
      ( A ) LENGTH: 10 amino acids
      ( B ) TYPE: amino acid
      ( D ) TOPOLOGY: circular ( i i ) MOLECULE TYPE: peptide ( i x ) FEATURE:
      ( A ) NAME/KEY: Peptide
      ( B ) LOCATION: 10
      ( D ) OTHER INFORMATION: /note="Xaa =Amino acid is
         amidated at C-terminal."

( x i ) SEQUENCE DESCRIPTION: SEQ ID NO:2:

Gly Ala Ala Arg Gly Asp Thr Pro Glu Xaa
   1               5                   10

( 2 ) INFORMATION FOR SEQ ID NO:3:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

Gly Arg Gly Asp Ser Pro
   1               5

( 2 ) INFORMATION FOR SEQ ID NO:4:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:4:

Gly Arg Gly Glu Ser Pro
   1               5

( 2 ) INFORMATION FOR SEQ ID NO:5:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:5:

Gly Arg Gly Asp Ser Pro Lys
1               5

COMPOSITIONS THAT INHIBIT WOUND CONTRACTION AND METHODS OF USING SAME

BACKGROUND OF THE INVENTION

1. FIELD OF THE INVENTION

This invention relates generally to the field of tissue regeneration and more specifically to wound healing.

2. BACKGROUND INFORMATION

Wound healing is a necessary physiological response to a wound in a subject. Following a cutaneous wound, for example, epithelial cells migrate into the wounded area to cover the site of injury. At the same time, skin fibroblasts, which normally are relatively quiescent, begin to divide, migrate into the wound and secrete a collagen matrix. The fibroblasts, which acquire myocyte-like characteristics, cause contraction of the collagen matrix, which brings the edges of the wound together and closes the wound.

In normal healing of a small wound, contraction results in the production of a minimal cosmetic scar. When larger wounds heal, however, excessive scar formation can occur and can result, for example, in loss of joint motion or major body deformation (Grinnell, *J. Cell Biol.* 124:401– 404 (1994); Clark and Henson, *The Molecular and Cellular Biology of Wound Repair* (Plenum Press 1988)). Thus, while wound contraction is a necessary element of wound repair, abnormal wound contraction can lead to excessive scarring and the formation of pathological contractures and constrictures.

Contractures can occur, for example, in burn patients and can result in excessive morbidity. Similarly, constrictures can form when abnormal wound contraction occurs in a hollow organ such as the esophagus (Grinnell, supra, 1994). Since abnormal wound healing can cause contractures and constrictures, which can result in loss of function and physical deformity, it can be desirable to control wound contraction so as to prevent excessive scar formation and allow normal tissue regeneration. Thus, a need exists to develop methods for effectively reducing or inhibiting wound contraction in a subject. The present invention satisfies this need and provides related advantages as well.

SUMMARY OF THE INVENTION

The present invention provides methods for reducing or inhibiting wound contraction in a subject having a wound comprising administering to the subject a pharmaceutical composition comprising a peptide or a polypeptide. The invention provides, for example, a method of reducing or inhibiting wound contraction comprising the administration of a pharmaceutical composition comprising a peptide having more than three consecutive basic amino acids. The invention also provides a method of reducing or inhibiting wound contraction comprising the administration of a pharmaceutical composition comprising decorin.

DETAILED DESCRIPTION OF THE INVENTION

Figure 1:
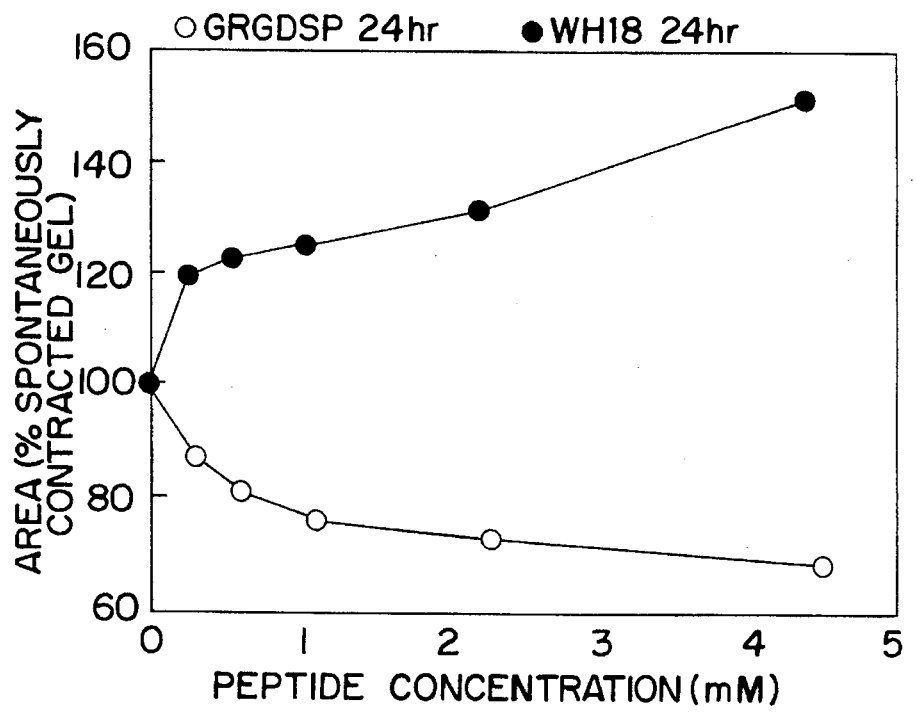
FIG. 1 demonstrates the dose-response effect of two peptides, WH18 (table 1) and GRGDSP (SEQ ID NO: 3), in the collagen gel contraction assay. Peptides were added to the gels at the indicated concentration and incubated for 24 hr. Following incubation, the area of the gel was determined by planimetry. The area of the experimental gel was normalized to the amount of contraction of a control gel, which was incubated for 24 hr without any peptide, and expressed as the percent of control gel contraction.

The present invention provides methods of reducing or inhibiting wound contraction in a subject comprising administering to the subject a pharmaceutical composition comprising a peptide or a polypeptide. The invention provides, for example, a method of reducing or inhibiting wound contraction comprising the administration of a pharmaceutical composition comprising a peptide having more than three consecutive basic amino acids. Peptides that can be useful for reducing or inhibiting wound contraction include, for example, the peptides shown in Table 1, below.

As used herein, the term "wound contraction" refers to a step in the process of wound healing, wherein the edges of the wound are brought together in an attempt to close the wound (see, for example, Grinnell, *J. Cell Biol.* 124: 401–404 (1994)). As used herein, the term "wound healing" is used in its broadest sense to mean the entire process from the time a wound is incurred until the physiologic characteristics associated with wound healing are completed. Wound contraction, for example, is part of the wound healing process. Thus, a composition that reduces or inhibits wound contraction can enhance wound healing. It is recognized that wound healing does not necessarily result in the wounded tissue attaining the same level of organization as was present prior to the time of wounding.

As used herein, the terms "reduce" and "inhibit" have their common meanings. The terms are used together, here, to avoid any ambiguity as to the extent to which a composition of the invention acts. It is recognized, for example, that a composition as disclosed herein can decrease the amount of wound contraction below a level that is detectable using a particular assay such as the gel contraction assay. In this situation, one would be unable to determine whether the amount of wound contraction was reduced to a very low level or inhibited such that no contraction was occurring. The use of these terms together precludes the need to distinguish these events.

As used herein, the term "peptide" means a sequence of about four to about thirty amino acids. In general, a peptide useful in the invention is a nonnaturally occurring peptide such as the chemically synthesized peptides shown in Table 1, below. A peptide of the invention is characterized, in part, by containing a sequence of more than three consecutive basic amino acids such as arginine or lysine residues, which can be (D)- or (L)-amino acids. WH18, which consists of eighteen amino acids containing therein a sequence of five consecutive Arg residues in the D-amino acid form (see Table 1, below, where (D)R indicates D-arginine), is an example of a peptide useful in practicing the invention. While the cell attachment and wound healing characteristics of WH18 are known, it was not known prior to the present disclosure that WH18 can reduce or inhibit wound contraction.

Wound contraction is a necessary element of wound repair (Grinnell, supra, 1994; see, also, "The Molecular and Cellular Biology of Wound Repair" pp. 11–12 (Clark and Henson, eds.; Plenum Press 1988). Nevertheless, it can be desirable to reduce or inhibit the rate of wound contraction to allow maximal tissue regeneration and to minimize undesirable scar formation and incomplete or inadequate formation of the dermis (see, for example, U.S. Pat. No. 4,947,840, which describes the application of a biodegradable material to significantly delay or arrest the rate of wound contraction).

The collagen gel contraction assay is a well recognized in vitro model that provides results predictive of wound contraction in vivo (see, for example, Grinnell, supra, 1994; see, also Tomasek and Ariyama, *Anat. Rec.* 234:153–160 (1992). As disclosed herein, the gel contraction assay was used to demonstrate that various peptides can effectively reduce or inhibit wound contraction (see Example II). Cells were incorporated into collagen in solution and the cell-collagen mix was allowed to gel. The gel was then contacted with medium containing a peptide that was being examined for activity. Using the gel contraction assay, peptides that can reduce or inhibit contraction of the gel were identified and the magnitude of gel contraction was measured (see, for example, FIG. 3). The gel contraction assay also was used to show that a polypeptide such as decorin effectively reduced or inhibited gel contraction (Example II). The assay was performed essentially as described for the assay of peptide activity, except that the polypeptide was incorporated into the collagen gel.

The effect of a peptide or polypeptide on the rate and extent of wound contraction also can be evaluated using an in vivo system (see Example III). The in vivo assay can be used as a primary screening assay to identify a peptide or polypeptide that reduces or inhibits wound contraction or can be a secondary screening assay to further define the effectiveness of a peptide or polypeptide that reduces or inhibits gel contraction. The in vivo model is particularly useful for determining an effective dose of a peptide or a polypeptide that can reduce or inhibit wound contraction.

Although the mechanisms underlying wound contraction and gel contraction are not known, integrins, which mediate cell binding to extracellular matrix and, perhaps, to other cells (Hemler, *Ann. Rev. Immunol.* 8:365–400 (1990)), may have a role. A role for integrins in wound contraction is suggested by experiments showing that administration of polyclonal and monoclonal antibodies against the $\beta_1$ subunit of the $\alpha_2\beta_1$ collagen receptor inhibited gel contraction in vitro (Tomasek and Akiyama, supra, 1992). Similarly, peptides containing an arginine-glycine-aspartic acid (RGD) sequence are known to prevent or disrupt integrin mediated cell-matrix attachment when present in solution (see, for example, U.S. Pat. No. 4,792,525; see, also, Dedhar et al., *J. Cell Biol.* 104:585–593 (1987); Cardarelli et al., *J. Biol. Chem.* 267:23159–23164 (1992)) and, therefore, may be expected to inhibit collagen gel contraction. However, an RGD peptide, GRGDSP (SEQ ID NO: 3), enhanced gel contraction, whereas a nearly identical peptide, GRGESP (SEQ ID NO: 4), which substitutes glutamic acid for aspartic acid in the RGD sequence, inhibited contraction of collagen gels (Grinnell et al., *Exp. Cell Res.* 182:668–672 (1989); Grinnell, U.S. Pat. No. 4,957,902). Thus, it is unclear from these results whether or to what extent integrins are involved in wound contraction.

Development of an effective method for controlling wound contraction is further complicated by the effect of growth factors on wound contraction. For example, TGFβ stimulates wound contraction (Fukamizu and Grinnell, *Exp. Cell Res.* 190:276–282 (1990) and, in addition, may promote the differentiation of fibroblasts into myofibroblasts (Ronnov-Jessen and Petersen, *Lab. Invest.* 68:696–707 (1993); Desmouli et al., *J. Cell Biol.* 122:103–111 (1993)). In addition, platelet-derived growth factor (PDGF; Clark et al., *J. Clin. Invest.* 84:1036–1040 (1989)), acidic fibroblast-derived growth factor (acidic FGF; Mellin et al., *Growth Fact.* 7:1–14 (1992); Dubertret et al., *J. Invest. Dermatol.* 97:793–798 (1991)), basic fibroblast-derived growth factor (basic FGF; Stenberg et al., *J. Surg. Res.* 50:47–50 (1991)), gamma interferon (Gillery et al., *Eur. J. Cell Biol.* 57:244–253 (1992)) and angiotensin II (Burgess et al., *Circ. Res.* 74:291–298 (1994)) can affect wound contraction.

Integrins can interact with the basic region of peptides. For example, Ruoslahti et al. reported that $\alpha_v\beta_5$ and $\alpha_v\beta_3$ integrin bind to the basic region of the HIV tat protein (see WO 92/14755) and Savage et al. (*J. Biol. Chem.* 265:11766–11772 (1990)) reported that peptides that contained both an RGD sequence and a basic amino acid sequence bound to $GPII_bIII_a$ with greater avidity than did peptides containing only the RGD sequence. However, there have been no reports suggesting that these or other peptides comprising more than three consecutive basic amino acids can reduce or inhibit wound contraction.

A basic polyamino acid such as polyarginine or polylysine is another example of a peptide or, depending on its size, a polypeptide that can be used in the disclosed method to reduce or inhibit wound contraction. Polyarginine and polylysine support cell attachment on solid supports based on the positive charge resulting from the basic polyamino acid coating. (Sepulveda and Schlager, *Meth. Enzymol.* 93:260–270 (1983). In view of the integrin mediated cell attachment properties of cells in vivo, administration of a basic polyamino acid to a wound in vivo would not be expected to inhibit cell attachment or to reduce or inhibit wound contraction.

Oral administration of dietary supplements that contain arginine can promote wound healing (see, for example, Kirk et al., *Surgery* 114:155–159 (1993); Daly et al., *Surgery*

112:56–67 (1992); Barbul et al. *J. Surg. Res.* 38:328–334 (1985)). However, there have been no reports to suggest that oral administration of polyarginine can reduce or inhibit wound contraction.

A peptide or polypeptide useful in the invention can be chemically synthesized using, for example, an automated synthesizer (see Example I). Selective modification of a reactive group such as an amino acid side chain or an N- or C-terminal group in a peptide can impart desirable characteristics to a peptide of the invention. A peptide can be manipulated while still attached to the resin following chemical synthesis or after cleavage from the resin to obtain, for example, an N-terminal modified peptide such as an acetylated peptide. Peptides also can be synthesized containing the C-terminal carboxy group or a C-terminal amide using methods known in the art (see, for example, Bodanszky, *Principles of Peptide Synthesis* (Springer-Verlag 1984), which is incorporated herein by reference). The choice of modifications made to the reactive groups present on a peptide will be determined by the characteristics that the skilled artisan requires in the peptide. In addition, it can be desirable to cyclize a peptide using any of various methods (see Example I). A newly synthesized peptide can be purified using a method such as reverse phase high performance liquid chromatography (RP-HPLC), as described in Example I, or other methods of separation based on the size or charge of the peptide. Similarly, the structure of a peptide useful in the invention can be characterized using well known methods such as amino acid sequence analysis or mass spectrometry (see Example I).

As used herein, the term "amino acid" is used in its broadest sense to include naturally occurring proteogenic amino acids and imino acids as well as nonnaturally occurring amino acids and imino acids and analogs and mimics thereof. As used herein, the term "proteogenic" indicates that the amino acid can be incorporated into a protein in a cell through well known metabolic pathways. In view of this broad definition of an amino acid, one skilled in the art would know that reference herein to an amino acid, unless specifically indicated otherwise, includes, for example, naturally occurring proteogenic (L)-amino acids, (D)-amino acids, chemically modified amino acids such as amino acid analogs, naturally occurring non-proteogenic amino acids such as norleucine, and chemically synthesized compounds having properties known in the art to be characteristic of an amino acid.

The choice of including an (L)- or a (D)-amino acid in a peptide useful in the invention depends, in part, on the desired characteristics of the peptide. For example, the incorporation of one or more (D)-amino acids can confer increased stability on the peptide in vitro or in vivo and can allow the peptide to remain active in the body for an extended period of time. The incorporation of one or more (D)-amino acids also can increase or decrease the pharmacological activity of the peptide as determined using the gel contraction assay (Example II) or other in vitro or in vivo assays for determining the effectiveness of a peptide for enhancing wound healing or for reducing or inhibiting wound contraction. The skilled artisan can determine the desirable characteristics required of a peptide by taking into consideration, for example, the age and general health of a subject.

The present invention also provides methods of reducing or inhibiting wound contraction in a subject having a wound comprising administering to the subject a pharmaceutical composition comprising a polypeptide. The invention provides, for example, a method of reducing or inhibiting wound contraction comprising the administration of a pharmaceutical composition comprising decorin. As used herein, the term "polypeptide" means a sequence of at least about thirty amino acids. It is recognized, however, that the distinction between a "large" peptide and a "small" polypeptide is not well defined. Thus, arbitrary limits are provided herein for convenience of discussion.

A polypeptide useful in the disclosed method of reducing or inhibiting wound contraction can be obtained, for example, by chemical synthesis or using methods of biochemical purification as described for decorin (see Example I). The polypeptide can be produced by a cell that naturally expresses the polypeptide or by a cell that expresses a recombinant DNA molecule encoding the polypeptide. The term "polypeptide" is intended to include active fragments of the polypeptide, which are amino acid sequences comprising a portion of the entire amino acid sequence of the polypeptide, provided that the amino acid sequence retains at least one activity of the polypeptide, including the ability to reduce or inhibit wound contraction. An active fragment of a polypeptide can be a peptide having about four to about thirty amino acids as described herein.

Decorin is an example of a polypeptide that can be useful in the disclosed method of reducing or inhibiting wound contraction, as is an active fragment of decorin, provided the active fragment includes that portion of decorin that is involved in reducing or inhibiting wound contraction. Decorin, which also is known as PG-II or PG-40, is a proteoglycan that is produced by fibroblasts. Decorin has a core protein structure having a molecular weight of about 40 kilodaltons (kDa). The core protein has been sequenced (Krusius and Ruoslahti, Proc. Natl. Acad. Sci. USA 83:7683 (1986); Day et al. Biochem. J. 248:801 (1987)). Decorin contains a single glycosaminoglycan chain of a chondroitin sulfate/dermatan sulfate type (Pearson, et al., J. Biol. Chem. 258:15101 (1983)). Decorin binds to type I and type II collagen and affects fibril formation by these collagens (Vogel, et al., Biochem. J. 223:587 (1984); Schmidt et al., J. Cell Biol. 104:1683, (1987)). Decorin also binds to TGFβ and can neutralize the activity of TGFβ (Yamaguchi et al., *Nature* 346:281 (1990)).

As used herein, the term "decorin" is used in its broadest sense to include a native decorin composition as well as a modified decorin, provided that the modified decorin is a functional equivalent of native decorin. The decorin core protein, which is a decorin polypeptide that is not substantially substituted with glycosaminoglycan, or an active fragment thereof can be useful for reducing or inhibiting wound contraction. Decorin can be rendered glycosaminoglycan-free by mutation, for example, or by producing recombinant decorin in cells that do not attach glycosaminoglycan chains to a core protein.

Functional equivalents of decorin also can be useful for reducing or inhibiting wound contraction. Functional equivalents of decorin include, for example, a decorin polypeptide that is structurally different from native decorin but retains a functional activity that is similar to a functional activity characteristic of native decorin. An active fragment of decorin is another example of a functional equivalent of decorin. A functional equivalent of decorin also can be a decorin polypeptide that is modified, for example, by the addition of one or more side chains such as a lipid or a carbohydrate chain or by chemical modification such as phosphorylation of a side chain, provided that the modification does not interfere substantially with the ability of decorin to reduce or inhibit wound contraction as disclosed herein.

Decorin has been used to prevent TGFβ-induced cell proliferation and extracellular matrix production (see, for example, Yamaguchi and Ruoslahti, *Nature* 336:224(1988); Border et al., *Nature* 360:361 (1992)). Decorin can bind TGF and can inhibit TGFβ activities. Decorin also can bind collagen and affect collagen fibril formation. However, there have been no reports suggesting that decorin can reduce or inhibit wound contraction and the binding of decorin to collagen, while apparently necessary, is not sufficient to reduce or inhibit gel contraction. For example, denatured decorin binds collagen to the same extent as nondenatured decorin. However, unlike native decorin, denatured decorin does not affect fibril structure. While denatured decorin retains some ability to inhibit gel contraction, the level of inhibition is significantly less than that seen with intact decorin.

Two proteoglycans, biglycan (Fisher et al., *J. Biol. Chem.* 264:4571 (1989)) and fibromodulin (Oldberg et al., *Embo J.* 8:2601, (1989), have core protein structures that consist of amino acid sequences that are closely related to that of decorin. Decorin, biglycan and fibromodulin comprise a protein family that is characterized, in part, by containing a leucine-rich repeat of about 24 amino acids. Similar repeats occur in other proteins, which, with decorin, biglycan and fibromodulin, comprise a superfamily of proteins (Ruoslahti, *Ann. Rev. Cell Biol.* 4:229, (1988); McFarland et al., *Science* 245:494 (1989)). Biglycan and fibromodulin also can have a functional activity similar to decorin. For example, biglycan can bind to collagen in the gel contraction assays. Since biglycan and fibromodulin are characterized, in part, as having a functional activity similar to decorin, these polypeptides are further examples of functional equivalents of decorin.

Functional equivalents of decorin or of other peptides useful in the invention can be identified using the assays described in Examples II and III. For example, a polypeptide or a peptide that is thought to be a functional equivalent of decorin can be added to or incorporated into the gel described in Example II and a time course study of gel contraction can be performed. A polypeptide or peptide that is, in fact, a functional equivalent of decorin can be identified by its ability to reduce or inhibit gel contraction. In addition, a functional equivalent of decorin can be identified using the in vivo assay described in Example III.

Pharmaceutical compositions comprising a peptide or a polypeptide useful for reducing or inhibiting wound contraction and a pharmaceutically acceptable carrier can be administered to a subject having a wound. Pharmaceutically acceptable carriers are well known in the art and include aqueous solutions such as physiologically buffered saline or other solvents or vehicles such as glycols, glycerol, vegetable oils (e.g., olive oil) or injectable organic esters. A pharmaceutically acceptable carrier can be used to administer a peptide or polypeptide useful in the invention to a cell in vitro or to a subject in vivo.

A pharmaceutically acceptable carrier can contain a physiologically acceptable compound that acts, for example, to stabilize the peptide or polypeptide or to increase or decrease the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and sorbic acid. One skilled in the art would know that the choice of a pharmaceutically acceptable carrier, including a physiologically acceptable compound, depends, for example, on the route of administration of the peptide or polypeptide and on the particular physico-chemical characteristics of the specific peptide or polypeptide. For example, a physiologically acceptable compound such as aluminum monosterate or gelatin is particularly useful as a delaying agent, which prolongs the rate of absorption of a pharmaceutical composition administered to a subject.

A pharmaceutical composition comprising an effective amount of a peptide or polypeptide useful for reducing or inhibiting wound contraction can be administered to a subject having a wound by various routes including, for example, topically, orally or parenterally, such as intravenously, intramuscularly, subcutaneously, intraperitoneally or by passive or facilitated absorption through the skin using, for example, a skin patch or transdermal iontophoresis, respectively. Topical administration can be passive, for example, by direct application of an ointment or powder, or active, for example, using a nasal spray or inhalant. Where the composition is administered as a topical spray, one component of the composition is an appropriate propellant. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

A pharmaceutical composition useful in the disclosed method comprises an effective amount of a peptide or polypeptide useful for reducing or inhibiting wound contraction, which is about 0.01 to 100 mg/kg body weight. As used herein, the term "effective amount" means a dose of a peptide or polypeptide that can reduce or inhibit wound contraction in a subject. An effective amount can be determined using methods known to those in the art, including the method described in Example III. The total effective amount can be administered to a subject as a single dose, either as a bolus or by infusion over a relatively short period of time, or can be administered using a fractionated treatment protocol, in which the multiple doses are administered over a more prolonged period of time. One skilled in the art would know that the amount of a peptide or a polypeptide required to obtain an effective dose in a subject depends on many factors including the age and general health of the subject as well as the route of administration and the number of treatments to be administered. In view of these factors, the skilled artisan would adjust the particular dose so as to obtain an effective amount for reducing or inhibiting wound contraction in a subject.

The following examples are intended to illustrate but not limit the present invention.

EXAMPLE I

PREPARATION OF PEPTIDES AND DECORIN

This example describes methods for synthesizing a peptide of the invention and for preparing decorin.

A. Peptide synthesis:

The peptides shown in Table 1 were synthesized by solid phase synthesis (Steward, J. M. and Young, J. D., Solid Phases Peptide Synthesis, 2nd ed.; Pierce Chemical Co., Rockford, Ill., 1984) using an Applied Biosystems Model 431A automated synthesizer (Applied Biosystems, Inc.; Foster City Calif.). Carboxamide peptides were synthesized with p-methlybenzhydrylamine resin. Peptides with C-terminal acids were synthesized with chloromethylated resin. N-terminal tertbutyloxycarbonyl protection was employed for all amino acids. Boc-Ala-OH, Boc-Arg(Tos)-OH, Boc-(D)Arg-OH, Boc-Asp(OcHx)-OH, Boc-Gly-OH, Boc-Gln-OH, Boc-Glu(OFm)-OH, Boc-Ile-OH, Boc-Lys( 2-chloro-Z)-OH, Boc-Pro-OH, Boc-Ser-(Bzl)-OH, Boc-Thr(Bzl)-OH and Boc-Tyr(2-bromo-Z)-OH were obtained from Bachem Inc. (Torrance, Calif.) ("Z" is benzyloxycarbonyl). Dicyclohexylcarbodiimide and hydroxybenzyltriazole were used in the coupling reactions, which were monitored by the ninhydrin test.

TABLE 1

PEPTIDES

| NAME | Amino Acid Sequence* |
|---|---|
| WH18 | G—{(D)R}$_5$—GGG—(D)R—GDSPASSK |
| WH18ILE | G—{(D)R}$_5$—GGG—(D)R—GDIPASSK |
| WH18RAD | G—{(D)R}$_5$—GGG—(D)R—ADSPASSK |
| 15P | YGRRRRRQRRRP (SEQ ID NO: 1) |
| 23N | GAARGDTPE—NH$_2$ (SEQ ID NO: 2) |

*Amino acid residues are indicated by their single letter code. (D)R indicates the D-amino acid form of arginine.
Bold print indicates the amino acid residues involved in the lactam bond; 23N is a cyclic peptide.

The peptides were removed from resin and deprotected with anhydrous hydrogen fluoride (HF; 10 ml/g resin-bound peptide) containing anisole (1 ml/g) at 0° C. for 60 min. After the HF was evaporated, the residue was washed with anhydrous ether and the crude peptides were extracted with water or with 15% aqueous acetic acid. The aqueous fractions were combined and lyophilized. For synthesis of the cyclic peptide, 23N, the lactam bridge was formed while the peptide was on the resin using the method described by Felix et al., Int. J. Pept. Prot. Res. 31:231 (1988) and by Felix et al., Int. J. Pept. Prot. Res. 32:441 (1988), each of which is incorporated herein by reference.

Peptides were purified using preparative reverse phase high performance liquid chromatography (RP-HPLC) on a C$_{18}$ silica gel column (Delta-Pak, 15 μm, 300A, 47×300 mm; Waters; Milford Mass.). Peptides were eluted using a linear acetonitrile gradient (0–40%) with a constant concentration of trifluoroacetic acid (0.1% v/v) over 20 min at a flow rate of 40 ml/min.

The purified peptides were analyzed by analytical RP-HPLC on C-18 Columns (5 μm, 300A, 4.5×250 mm; Vydac; Hesperia Calif.). The purified peptides, recovered by lyophilization of the HPLC fractions, were at least 95% pure. Elution of the peptides by analytical RP-HPLC utilized a binary solvent system consisting of water containing 0.1% trifluoroacetic acid (TFA) and acetonitrile containing 0.1% TFA as the organic modifier. The solvent programs produced linear gradients as follows: (1) 10% to 45% acetonitrile over 35 min with flow rate of 1.5 ml/min and (2) 0% to 70% acetonitrile over 30 min with flow rate of 1.5 ml/min.

All peptides were characterized by fast atom bombardment (FAB) mass spectroscopy and amino acid analysis. Peptide samples (1 mg) were hydrolyzed in 1 ml 6N constant boiling HCl. Samples were degassed and sealed under vacuum, then heated for 24 hr at 110° C.

B. Preparation of decorin:

Decorin was produced using decorin-expressing Chinese hamster ovary (CHO) cells as described in WO90/00194. Alternatively, larger scale productions of decorin were performed using CHO cells attached to microcarrier bead. Decorin-expressing CHO cells (WO 90/00194, which is incorporated herein by reference) were allowed to adhere to microcarrier beads, then were cultured in suspension. Once a seed culture of decorin-expressing cells was established, the fermentation reaction vessel was seeded and the growth phase of fermentation continued until the desired cell density was achieved. At that time, fresh medium was slowly perfused into the reactor vessel and conditioned medium was collected at a rate of about 80–85% of the reactor volume per day. Care was taken to separate cell-containing microcarriers from the perfusate so as not to lose decorin-producing cells. The harvest medium was incubated at 4° C. for 24 hr prior to filtration to remove particulate matter.

Decorin was purified from 40 l of cell culture medium. A solution of benzamidine and Na$_4$EDTA was added to a final concentration of 1× in the medium (100×solution is 100 mM benzamidine and 500 mM Na$_4$EDTA in 9M urea). The medium was filtered with Whatman #1 filter paper and the NaCl concentration was adjusted to 0.4M NaCl.

A Q-Sepharose column was prepared by washing 300 ml resin (Q-Sepharose fast flow gel; Pharmacia; Piscataway N.J.) in a fritted disc glass funnel with 10 column vol deionized water to remove ethanol. The Q-Sepharose was degassed and placed into a 10 cm×30 cm column with a flow adapter (Watson/Marlow Peristaltic Pump with 9.6 mm ID tubing). The bubble trap and pump were connected to the column, which then was equilibrated at a flow rate of 200 ml/min with 10 column vol buffer A (25 mM Tris, pH 7.8, 0.4M NaCl). UV absorbance at 280 nm, 1.0 AUFS (Absorbance units, full scale) was determined; the detector was set to zero using buffer A.

Cell culture medium was loaded onto the column at a flow rate of 200 ml/min and the flow through was collected. The column was washed with 1 l buffer A, then with 1.5 l buffer B (25 mM Tris, pH 7.8, 6M urea, 2 mM CHAPS), at a flow rate of 80 ml/min. The column was eluted with 1.5 l buffer C (25 mM Tris, pH 7.8, 6M Urea, 1M NaCl ) and one minute fractions were collected. The eluted peak was pooled, the volume was recorded (usually 1–1.5 l) and absorbance at 280 nm and at 260 nm was determined. The latter reading was used to detect RNA that coeluted with decorin on the Q-Sepharose column. One vol (equal to the pooled volume) 2M guanidinium-HCl (GuHcl) was added and the sample was loaded onto an Octyl-Sepharose column.

The Octyl-Sepharose column was prepared by washing 60 ml Octyl-Sepharose gel (Pharmacia) with 10 column vol deionized water in a sintered glass funnel to remove EtOH. The gel was degassed and placed in a 2.6 cm×30 cm water jacketed column with two flow adapters (Pharmacia), which compacted and retained the gel in position. The column was maintained at 25° C. with a refrigerated circulator. The UV monitor (280 nm) was connected and was set to zero with buffer D (0.1 NaOAc, pH 6.3, 1M GuHCl filtered with 0.2 μM acetate filter and degassed).

The fraction collected from the Q-Sepharose column was loaded onto the Octyl-Sepharose column at a flow rate of 3 ml/min and samples were collected at 2 min/fraction (6 ml/tube). The column was washed with one column vol buffer D, until the baseline was established, then with one column vol buffer E (0.1M NaOAc, pH 6.3, 2M GuHCl filtered with 0.2 μM acetate filter, then degassed) until the same baseline was established.

Decorin was eluted using 200 ml buffer F (0.1M NaOAc, pH 6.3, 3M GuHCl ) at a flow rate of 3 ml/min. A small amount of protein contaminant eluted with the decorin. An elution profile was performed on the fractions by determining the absorbance at 280 nm and 260 nm to show that most of O.D. 280 nm absorbance was due to decorin and not to RNA. The column then was stripped using 150 ml buffer G (0.1M NaOAc, pH 6.3, 4M GuHCl; filtered with 0.2 μM acetate filter, then degassed), to remove an unidentified 200 kDa protein and some histone proteins. The column was washed with 150 ml of buffer H (0.1M NaOAc, pH 6.3, 8M GuHCl filtered with 0.2M acetate filter, then degassed) to remove more host cell contaminating proteins.

The 3M GuHCl fraction containing decorin was diluted 1:10 with 50 mM NaPO$_4$, pH7.4/0.4M NaCl. A Q-Sepharose column (Pharmacia) was equilibrated with 50 mM NaPO$_4$ (pH 7.4)/0.4M NaCl and the diluted decorin solution was pumped (Minipuls 2 peristaltic pump with 1.52 ID PVC manifold tubing; Gilson; Middleton Wis. onto the column at a rate of 3 ml/min. The column was washed with five column vol of the same buffer, then decorin was eluted with 50 mM NaPO$_4$ (pH 7.4)/1.0M NaCl. The eluent was concentrated by ultrafiltration.

In some cases, decorin was reduced and alkylated. Briefly, 1 mg/ml decorin was incubated with 50 mM dithiothreitol (Sigma) for 2 hr at 37° C., followed by incubation with 125 mM iodoacetamide (Sigma; St. Louis Mo.) for 15 min at 37° C. Reduced and alkylated decorin was dialyzed with 4-1 l changes of PBS over 12 hr at 4° C. Decorin was quantitated by amino acid analysis.

EXAMPLE II

GEL CONTRACTION ASSAYS

This example describes gel contraction assays useful for determining the activity of a peptide or of a polypeptide to reduce or inhibit gel contraction.

A. Peptide Gel Contraction Assay:

CTT-18 cells, which are a normal human colon fibroblast cell line available from ATCC (#1459-CRL), were used in the gel contraction assays. Subconfluent CTT-18 cells were harvested by trypsinization, neutralized with soybean trypsin inhibitor, then washed several times with serum-free Dulbecco's modified Eagle's medium (DMEM). The cells were resuspended at $5\times10^6$ cells/ml in DMEM.

The collagen solution was prepared by combining the following reagents in the stated order: 1× DMEM, 1× insulin/transferrin/selenium (ITS; Collaborative Research; Bedford Mass.), 25 mM HEPES, 2.5 mg/ml rat tail collagen I (Collaborative Research). The solution was adjusted to pH 7.4 using 2M NaOH and deionized water was added to the appropriate final volume. Finally, 5×104 cells/ml (DMEM) were added to the solution and 0.6 ml of the combined solution was added to each well of a 24 well plate. The solution was allowed to gel for 1 hr at 37° C.

Peptides were diluted to 4.5 mM in 1× DMEM/1× ITS/ 1×penicillin/1×streptomycin and the solution was adjusted to pH 7.4. Each gel was overlayed with 0.6 ml peptide solution and the gel periphery was rimmed to release the gel from the edge of the well. The gels were incubated at 37° C. and each gel area was monitored daily by planimetry using a computerized planimetry program (Digitize, Macintosh).

In addition to determining the area of a gel, a replicate gel for each experimental condition was examined each day for cell viability. To determine cell viability, the overlay media was removed and replaced with 4 mg/ml collagenase type 2 (Worthington Biochemical; Freehold N.J.) in collagen digestion buffer (0.13M NaCl, 0.01M Ca acetate, 0.02M HEPES, pH 7.2). The sample was incubated at 37° C. until digestion was complete (about 1 hr). The solution was centrifuged at 3000 rpm in a microcentrifuge for 5 min and the pellet resuspended in trypsin/EDTA and incubated for 20 min at 37° C. The solution again was centrifuged, the pellet resuspended in 40 μl 10.4% trypan blue and the viable cells were counted in a hemocytometer. In general, the variations in cell viability were slight and it was unnecessary to correct the gel contraction results due to significant differences in cell viability.

Peptides WH18, WH18 WH18RAD, 15P (SEQ ID NO: 1) and 23N (SEQ ID NO: 2; see Table 1) were synthesized as described in Example I and were evaluated for gel contraction inhibiting activity. In addition, the activities of mono-, di- and tri-arginine (Sigma) and the peptides, GRGDSPK (SEQ ID NO: 5; Bachem) and GRGESP (SEQ ID NO: 4; Gibco BRL), were evaluated. The peptides GRGDSP (SEQ ID NO: 3) or GRGDSPK (SEQ ID NO: 5) produced similar results in this assay.

Figure 2:
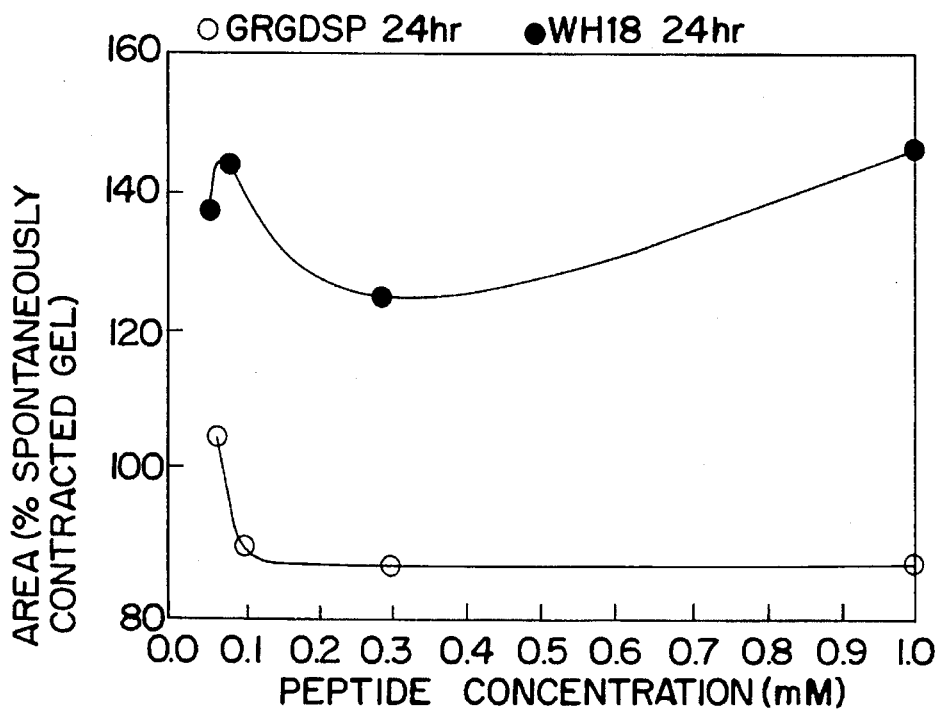
FIG. 2 demonstrates the dose-response effect of two peptides, WH18 (Table 1) and GRGDSP (SEQ ID NO: 6), over a narrower range of peptide concentrations as compared to FIG. 1. Values are expressed as percent of control gel contraction as described in FIG. 1.

A dose-response effect of WH18 and GRGDSP (SEQ ID NO: 3) is shown in FIGS. 1 and 2. Peptides were added to the gels at the concentrations indicated and incubated for 24 hr, then the gel area was determined. The gel area was normalized to the area of a control gel, which was allowed to contract in the absence of any peptide. As shown in FIG. 1, incubation of a gel with GRGDSP (SEQ ID NO: 3) resulted in a greater level of contraction than occurred in the absence of any peptide. In contrast, gel contraction was inhibited in a dose-dependent manner when the gel was incubated with WH18, which is an RGD-containing peptide having five consecutive (D)Arg residues. The effect of these peptides at low concentrations (0–1.0 mM peptide) also was determined (FIG. 2). Although a somewhat complex pattern of inhibition occurred at very low doses of WH18, gel contraction was inhibited at all concentrations of WH18 examined.

The activities of the peptides WH18Ile, WH18RAD and 15P were compared with WH18 and GRGDSPK (SEQ ID NO: 5) at a concentration of 1.0 mM at various times after addition of the peptides. As expected, GRGDSPK (SEQ ID NO: 5) did not inhibit gel contraction. In contrast, WH18, WH18Ile, WH18RAD and 15P each inhibited gel contraction by 20–25% as compared to contraction of a control gel (no peptide). Inhibition of contraction was evident within 18 hr after the addition of the peptides and the activity was maintained for at least as long as 96 hr, which was the longest time examined. The effects were independent of slight variations in cell viability and were reproduced with either the acetate or TFA forms of WH18, indicating the effect was not due to minor peptide contaminants.

Figure 3:
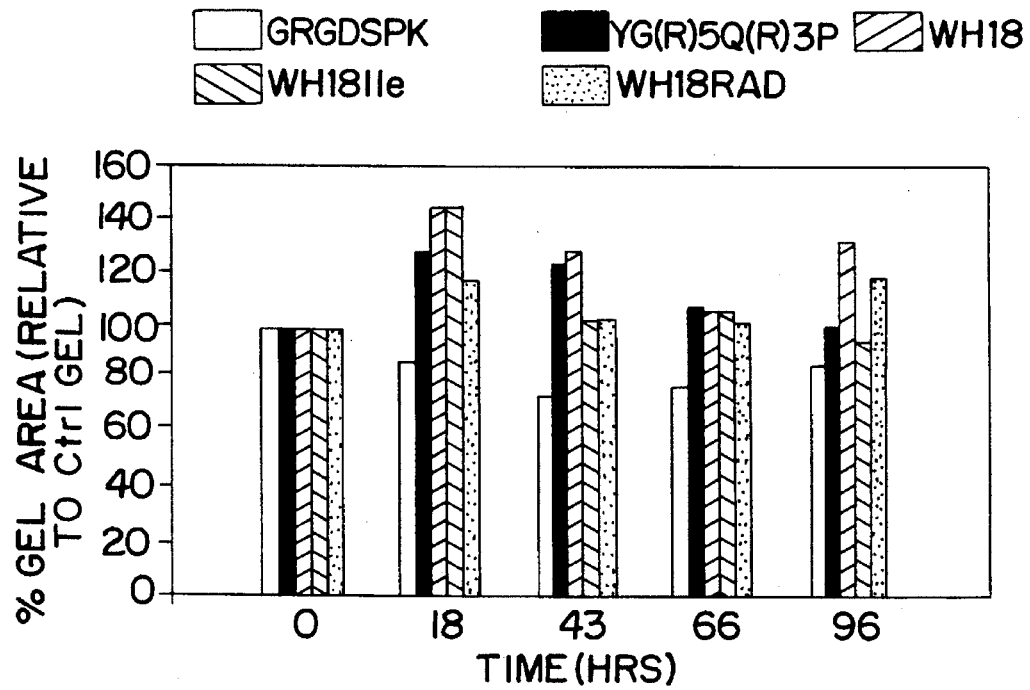
FIG. 3 demonstrates the activity of various peptides on gel contraction with time following addition of the peptides. WH18, WH18Ile, WH18RAD are shown in Table 1, as is $YG(R)_5Q(R)_3P$, where the peptide is designated 15P (SEQ ID NO: 1). Peptides were added at a concentration of 1 mM and gels were incubated for the indicated times. Gel area was determined by planimetry and is expressed as percent of control gel contraction.
Figure 4:
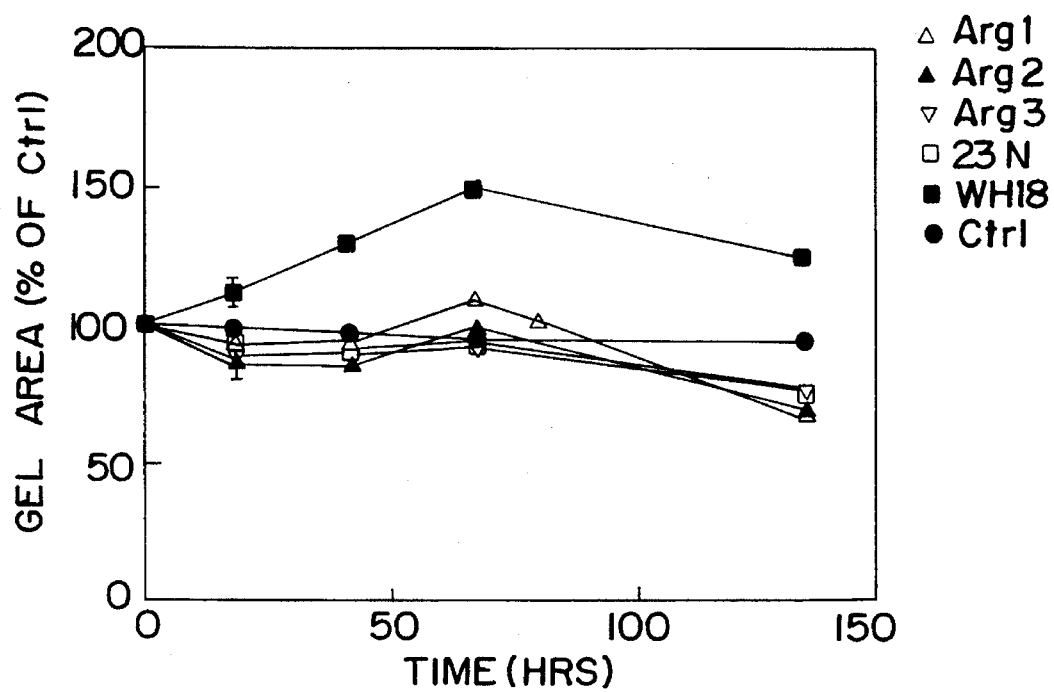
FIG. 4 demonstrates that mono-(Arg 1), di-(Arg 2) and tri-arginine (Arg 3) do not inhibit collagen gel contraction. 23N is $GAARGDTPE-NH_2$ (SEQ ID NO: 2). Ctrl indicates a control gel, which was incubated without any peptide. Collagen gels were incubated with the various molecules for the indicated time, then gel area was determined by planimetry. Results are shown as percent of control gel contraction.

The active peptides described above each contain a sequence of consecutive arginine residues. Since arginine is reported to have a role in wound healing, the activity of mono-, di- and tri-arginine were evaluated. As shown in FIG. 4, these molecules did not inhibit gel contraction. Also, to rule out the possibility that the RGD sequence was responsible for the effect on contraction, peptides WH18 and WH18RAD were compared. These peptides differ only in the substitution of an alanine residue in WH18RAD for the glycine residue in WH18. As shown in FIG. 3, the RGD sequence was not necessary to reduce or inhibit contraction. Thus, a peptide such as WH18, WH18RAD, WH18ILE or 15P, which has more than three consecutive Arg residues, is required to inhibit gel contraction.

B. Decorin Gel Contraction Assay:

The gel contraction assay also was used to demonstrate that a polypeptide, decorin, can inhibit gel contraction. NIH 3T3 mouse fibroblasts (ATCC #CRL 1658) and WI38 human fibroblasts (ATCC #CL75) were used in these assays and passaged in culture as prescribed.

Cells were collected by washing the cells with sterile PBS, then incubating the cells for 5 min at 37° C. with trypsin-EDTA (200 mg versene and 500 mg trypsin/liter Hank's balanced salt solution; Gibco/BRL; Gaithersburg Md.). Following incubation, cells were removed by aspiration with a pipet and DMEM supplemented with 10% FBS (BioWhittaker; Walkersville Md.) was added to neutralize the trypsin. Cells were centrifuged for 8 min at 1200 rpm, decanted, washed 3×with serum-free DMEM and resuspended in serumfree DMEM to the following concentrations: NIH 3T3 cells, $3.0\times10^6$ cells/ml; WI38 cells, $1.0\times10^6$ cell/ml.

The following reagents were added on ice to generate a total of 24 gels: 3.6 ml 5× DMEM (Gibco/BRL), 1.0 ml 1M HEPES (Sigma), 0.74 ml 0.5M NaOH, 2.0 ml cell suspension in serum-free DMEM, 7.6 ml rat tail collagen I (3.81 mg/ml; Collaborative Research). The collagen mixture was quickly added to a mixture of 4.8 ml decorin and water to yield the appropriate decorin concentration and 0.7 ml was added to each well of a 24 well microtiter dish that previously had been coated with 2% bovine serum albumin in PBS. The gels were allowed to solidify for 1 hr at 37° C. in a humidified incubator, then were released from the edges of the well by tapping or by rimming with a pipet tip.

Gels were transferred aseptically using forceps from the microtiter plate into a Nunc six well plate. Three gels were transferred into each 33 mm well. Prior to transfer, each well received 1 ng/ml TGFβ (from porcine platelets; R&D Systems; Minneapolis Minn.). In addition, 0.5% FBS was added to wells that were to receive gels containing NIH3T3 cells; WI38 cells did not require serum. The plates were rocked in a humidified incubator at 37° C. and 7% $CO_2$ for the length of the experiment. The area of the gels was measured daily using photographs from an image analyzer and planimetry.

Figure 5:
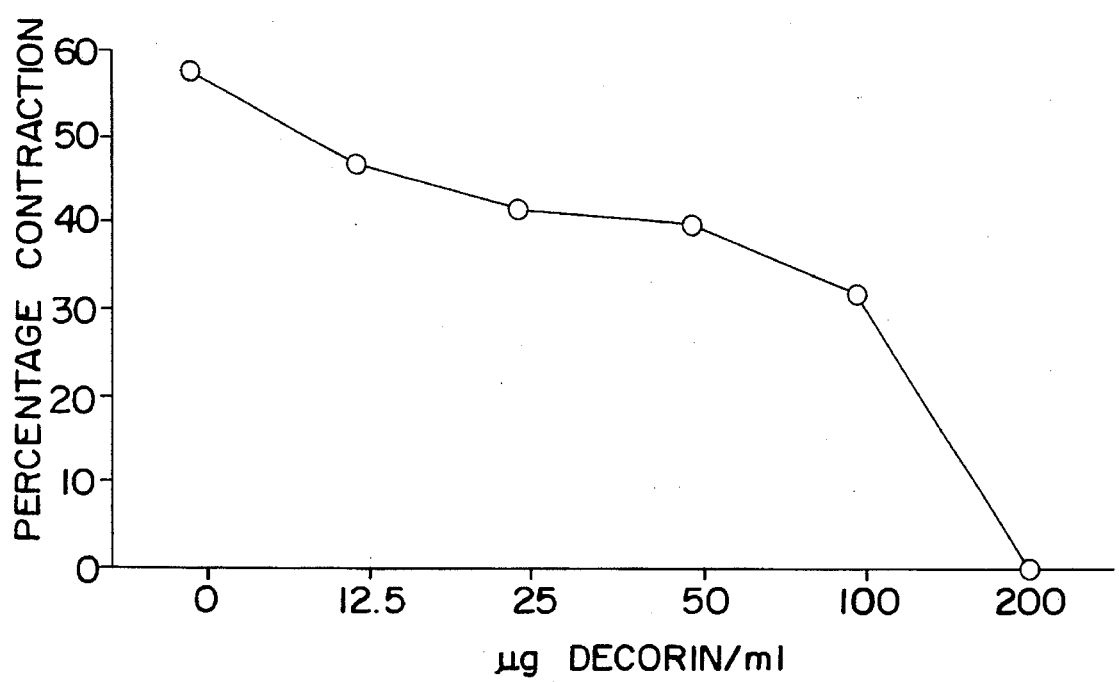
FIG. 5 shows a dose-response curve of contraction of a collagen/NIH3T3 cell gel after 24 hr in the presence of the indicated concentrations of decorin that were incorporated into the gel. Gels also were exposed to 1 ng/ml TGFB. Percent of gel contraction under the various conditions is shown.

A concentration of 1.0 ng/ml TGFB effected approximately 60% contraction of a collagen/NIH 3T3 gel after 24 hr of incubation (FIG. 5; 0 μg decorin). As shown, increasing concentrations of decorin in the gel reduced or inhibited gel contraction and, at 200 μg decorin, no gel contraction was observed. Decorin that had been reduced and alkylated also inhibited gel contraction (not shown). Similar results were obtained using collagen/WI38 cell gels.

Figure 6:
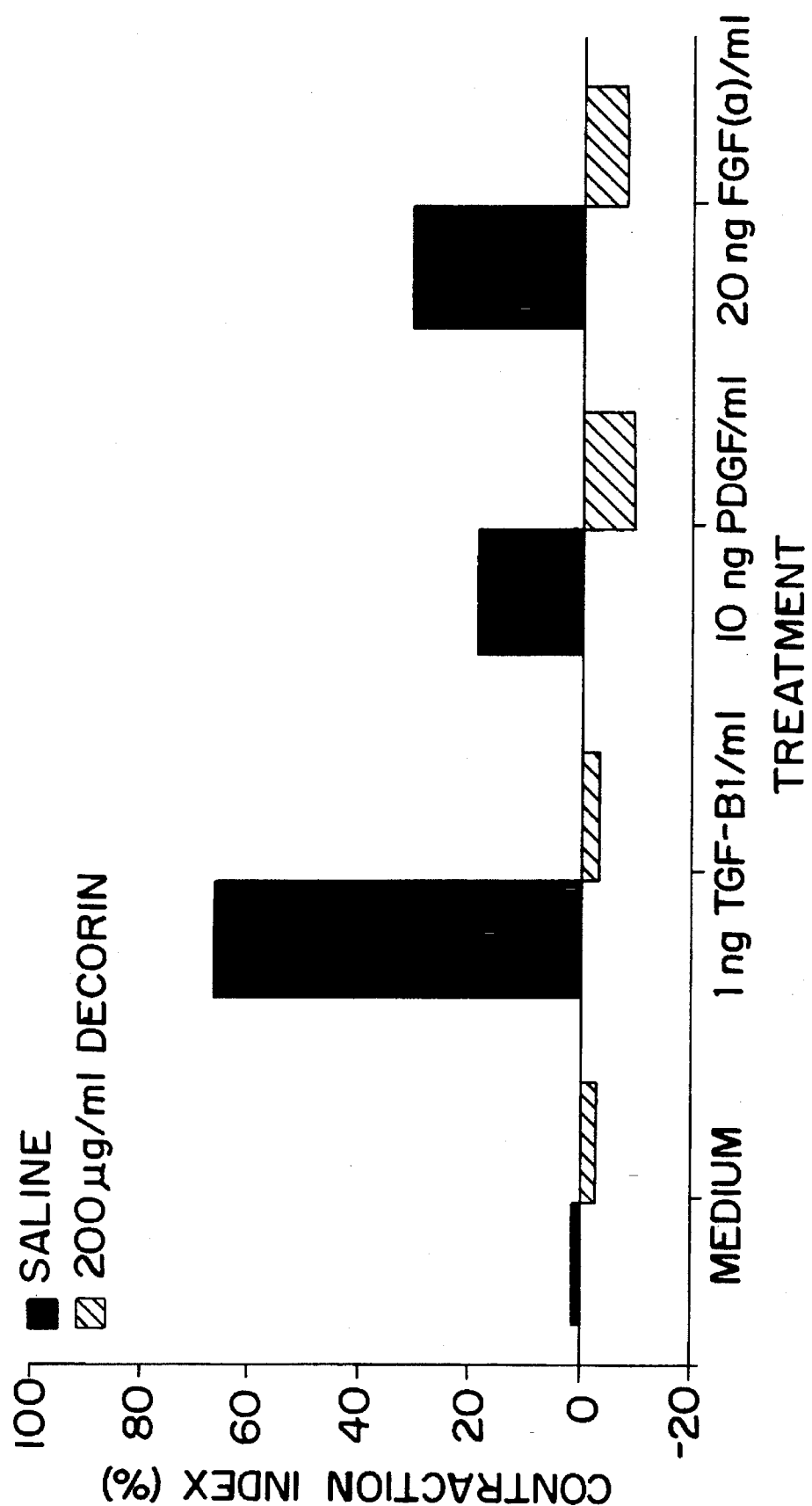
FIG. 6 demonstrates the effectiveness of 200 ug/ml decorin in reducing or inhibiting collagen/NIH/3T3 cell gel contraction in the presence of TGFβ, PDGF or acidic FGF (FGFa) at the indicated concentrations. Solid bars indicate contraction in the absence of decorin (Saline). Hatched bars indicate contraction in the presence of decorin, which was incorporated into the gel. Contraction index indicates the amount of gel contraction in the test conditions as compared to gel contraction in the absence of any growth factor or decorin (medium).

In some experiments, the effect of decorin on wound contraction in the presence of 1 ng/ml or 10 ng/ml PDGF (R & D Systems) or 20 ng/ml acidic FGF (R & D Systems) was examined. As shown in FIG. 6, 1 ng/ml TGFβ, 10 g/ml PDGF and 20 ng/ml acidic FGF (FGFa) increased the amount of collagen gel contraction above the control level. Incorporation of 200 μg decorin per ml gel reduced or inhibited the level of gel contraction that occurred in the presence of the growth factors. Thus, decorin effectively reduces or inhibits gel contraction in the presence of various different growth factors.

EXAMPLE III

ASSAY FOR WOUND CONTRACTION IN VIVO

This example describes a method for determining the effectiveness of a peptide or a polypeptide for inhibiting wound contraction in vivo.

Specific pathogen-free pigs are maintained in an accredited animal housing facility for two weeks prior to beginning an experiment. Animals are fed water and basal diet without antibiotics (Purina Control Factor) ad libitum. Temperature of the facility is maintained at 19°– 21° C. and a 12 hr light/12 hr dark cycle.

Experimental animals are clipped of hair using standard animal clippers. The skin on the back and both sides of an animal is prepared for wounding by washing with a non-antibiotic soap (Neutrogena®). Each animal is anesthetized by intramuscular injection of ketamine and inhalation of a mixture of Isoflurane, oxygen and nitrous oxide.

Six grids (8×8 cm) are made on the lateral paravertebral areas of each animal. Each grid is subdivided into 1×1 cm units. A scalpel is used to outline the grid and the scalpel incisions are stained with India ink to form a permanent tatoo (Alvarez and Biozes, *Clinics in Dermatology*, 2:54–67 (J. Lippincott 1984), which is incorporated herein by reference. A 4 $cm^2$ full-thickness wound (including subcutaneous fat) is excised from the center section of the grid and sterile gauze and pressure are used to stop the bleeding. The center grid is designated #1 and each of the surrounding adjacent grids is sequentially numbered #2 to #13 for identification.

Two full-thickness wounds on each animal are randomly assigned to a treatment group. Treatments, which can consist of various peptides or polypeptides suspected of being effective in reducing or inhibiting wound contraction or various concentrations of a peptide or polypeptide, are stored in coded containers so that "blind" assays can be performed. Wounds are treated at a desirable frequency such as one time or once per day for a period of time and are covered with a sterile dressing between application of the treatment. Control wounds are left untreated or are treated with the pharmaceutically acceptable carrier in which the test peptides or polypeptides are contained.

Wounds are examined prior to treatment and at various times after treatment. Dressings are removed and the wound outlines can be traced on a transparent sheet using a permanent marker. The wound area, perimeter, height and width can be obtained from the tracings using, for example, Jandel SigmaScan™ computer software and a digitizing tablet. Alternatively, the wound can be examined using video image analysis as described by Smith et al., *Wounds* 4:6–15 (1992), which is incorporated herein by reference.

Statistical analysis is performed using, for example, Statview®statistical analysis computer software and mixed analysis of variance. The term "mixed" in this context implies that some of the effects in the model are fixed and affect the mean values obtained, whereas other effects are random and affect the variation about the mean as well as correlations between the observations. These effects include, for example, the animal (random), location (fixed), treatment (fixed) and day (fixed). Interactions between these effects also can be included. The location term is included in the model to allay concerns about a faster healing rate depending on the location of the wound on the animal. Using this assay, the effectiveness of a peptide or a polypeptide for reducing or inhibiting wound contraction can be determined.

Although the invention has been described with reference to the examples provided above, it should be understood that various modifications can be made without departing from the spirit of the invention. Accordingly, the invention is limited only by the claims.

We claim:

1. A method for reducing or inhibiting wound contraction in a mammalian subject, comprising administering to said mammalian subject a pharmaceutical composition, comprising decorin and a pharmacologically acceptable carrier.

2. The method of claim 1, in which said mammalian subject is a human subject.

* * * * *

UNITED STATES PATENT AND TRADEMARK OFFICE
CERTIFICATE OF CORRECTION

PATENT NO. : 5,510,328
DATED : April 23, 1996
INVENTOR(S) : Polarek et al.

It is certified that error appears in the above-identified patent and that said Letters Patent is hereby corrected as shown below:

In column 2, line 26, please delete "TGFB" and replace with --TGFβ--.

In column 7, line 5, please delete "TGFB" and replace with --TGFβ--.

In column 9, Table 1, SEQ ID NO: 2, please delete "GAARGDTPE" and replace therefor with --GAARGDTPE--.

In column 10, line 17, please delete "100xsolution" and replace therefor with --100x solution--.

In column 10, line 61, please delete "GuHCl" and replace with --GuHCl;--

In column 11, line 8, please delete "0.2M" and replace with --0.2μM--.

In column 11, line 22, please delete "," and replace with --;--.

In column 11, line 49, please delete "5x104" and replace with --$5x10^4$--.

In column 11, line 54, please delete "1xpenicillin/1xstreptomycin" and replace therefor with --1x penicillin/1x streptomycin--.

In column 12, line 4, please delete "10.4%" and replace with --0.4%--.

In column 12, line 9, please delete "WH18" and replace with --WH18Ile--.

In column 13, line 10, please delete "serumfree" and replace with --serum-free--.

UNITED STATES PATENT AND TRADEMARK OFFICE
CERTIFICATE OF CORRECTION

PATENT NO. : 5,510,328
DATED : April 23, 1996
INVENTOR(S) : Polarek et al.

It is certified that error appears in the above-identified patent and that said Letters Patent is hereby corrected as shown below:

In column 13, line 11, please delete "3.0x106" and replace therefor with --$3.0 \times 10^6$--.

In column 13, line 12, please delete "cell/ml" and replace therefor with --cells/ml--.

In column 13, line 35, please delete "TGFB" and replace therefor with --TGF$\beta$--.

In column 13, line 46, please delete 10 g/ml" and replace therefor with --10 ng/ml--.

Signed and Sealed this

Fifteenth Day of December, 1998

Attest:

BRUCE LEHMAN

*Attesting Officer*  *Commissioner of Patents and Trademarks*